United States Patent [19]

Soda et al.

[11] Patent Number: 5,353,630
[45] Date of Patent: Oct. 11, 1994

[54] APPARATUS FOR TESTING MEMBRANE FILTER INTEGRITY

[75] Inventors: Fusao Soda, Koshigaya; Hidenobu Sawa, Suzuka, both of Japan

[73] Assignees: Memtec Japan Limited, Kanagawa; Filtec Corporation, Mie, both of Japan

[21] Appl. No.: 56,252

[22] Filed: Apr. 30, 1993

[30] Foreign Application Priority Data

May 1, 1992 [JP] Japan ................... 4-139831

[51] Int. Cl.$^5$ .......................................... G01N 15/08
[52] U.S. Cl. .................................................. 73/38
[58] Field of Search ....................................... 73/38

[56] References Cited

U.S. PATENT DOCUMENTS

| | | | |
|---|---|---|---|
| 4,614,109 | 9/1986 | Hofmann | 73/38 |
| 4,629,563 | 12/1986 | Wrasidlo | 210/500.34 |
| 4,701,861 | 10/1987 | Kauke | 73/38 |
| 4,744,240 | 5/1988 | Reichelt | 73/38 |
| 4,774,039 | 9/1988 | Wrasidlo | 264/41 |
| 4,872,974 | 10/1989 | Hirayama et al. | 73/38 X |
| 4,881,176 | 11/1989 | Kononov | 73/38 X |
| 5,064,529 | 11/1991 | Hirayama et al. | 73/38 X |

Primary Examiner—Hezron E. Williams
Assistant Examiner—Joseph W. Roskos
Attorney, Agent, or Firm—Knobbe, Martens, Olson & Bear

[57] ABSTRACT

A membrane filter integrity test system includes a large volume mass-flow controller for rapidly supplying a larger amount of fluid to a primary side of a membrane filter under test, a small volume mass-flow controller for supplying a relatively small amount of fluid to the primary side of the membrane filter. The operation of the large volume mass-flow controller is stopped when the pressure at the primary side of said membrane filter reaches a predetermined level. This predetermined pressure is detected by a pressure sensor which senses the pressure at the primary side of the membrane filter. The pressure sensor responsively generates a detection signal corresponding to the sensed pressure at the primary side of the membrane filter. A main controller responsive to the detection signal from the pressure sensor controls the small volume mass-flow controller in a negative feedback loop manner for controlling the supply of fluid to the primary side of the membrane filter so that the pressure on the primary side of the filter is maintained at the predetermined value.

6 Claims, 3 Drawing Sheets

APPARATUS FOR TESTING MEMBRANE FILTER INTEGRITY

FIELD OF THE INVENTION

The present invention relates to an improved apparatus for testing the perfection or integrity of a membrane filter, and more particularly to a computer controlled membrane filter integrity test system for testing the integrity of a membrane filter with higher precision and reliability by utilizing means for precisely controlling a pressure applied to the membrane filter.

BACKGROUND OF THE INVENTION

Membrane filters having a number of pores are used in a wide variety of industries such as pharmaceutical medical, electronics or food industries for sterilizing liquids, for example, whenever heat sterilization is impossible because of damage to the liquid itself. By way of example, the pore size of such membrane filter may be approximately 0.2 micrometer, and the pore density may be approximately $4 \times 10^9$ pores per square centimeter.

One of the ultimate purposes of using this kind of membrane filter is, in the pharmaceutical industry, for example, to prevent bacteria in certain liquids from passing through the filter, i.e., from a primary side to a secondary side of the membrane filter. Therefore, to evaluate the membrane filter characteristics, a direct test which measures the ratio of bacteria in the primary side and the secondary side of the membrane filter bacteria may be employed. This test is called a bacteria challenge test in the industry. Unfortunately, the bacteria challenge test, if performed in a literal manner, is subjected to a serious drawback in that to determine the ratio of bacteria between the primary side and the secondary side of the filter requires a measurement on the secondary side of the filter. The measurement on the secondary side of the filter will introduce the danger of secondary impurities, for example, further bacteria in the already sterilized liquid. To overcome this drawback, the bacteria challenge test requires utmost care and expensive facilities to minimize the danger of introducing secondary impurities. Moreover, the bacteria challenge test requires a considerably long time. Thus, the bacteria challenge test is not practical whenever the filter has to be tested in a cost effective manner.

Therefore, various types of test systems for testing the integrity of a membrane filter using other types of test methods and without using the bacteria challenge test are known in the art. These tests are performed without measurement on the secondary side of the membrane filter to prevent the introduction of impurities on the secondary side. Then these tests are validated with respect to the bacteria challenge test if there is sufficient correlation with the bacteria challenge test.

One of the conventional membrane filter perfection test systems involves recording a curve of increasing pressure on the primary side of the membrane filter under test on a chart sheet by a pen recorder. This conventional test system operates in two modes; i.e., a bubble point mode and a pressure hold mode.

The bubble point testing is generally used in order to test the integrity of the membrane filter to verify the fact that there are no pores having a size exceeding a certain predetermined limit. In this mode, a gas pressure is provided to a wetted membrane filter to be tested at its primary side to create a pressure difference across the membrane filter. The secondary side of the membrane filter is introduced to a container filled with liquid for easy detection of bubbles. The gas pressure on the primary side is gradually increased, which causes more and more gas to permeate through the filter as the pressure keeps mounting. Initially, the rate of gas flow measured on the secondary side of the filter is proportional to the increasing gas pressure on the primary side. As soon as the rate of gas flow measured on the secondary side of the membrane filter increases at a greater rate than does the gas pressure in the primary side, as indicated by a substantial increase in the quantity of gas bubbles escaping, the bubble point has been reached. This bubble point is read from the chart of increasing pressure.

In the prior art, however, the bubble point is determined visually, which is subjective to an operator of the test system. It is especially difficult to accurately determine the bubble point when testing a large capacity membrane filter, such as a cartridge type membrane filter, since a bubble will start even in a diffusion region which is less than the bubble point. As a result, the bubble point thus determined is usually at a point which is substantially lower than the time point specified by a manufacturer. Furthermore, the curve of increasing pressure varies depending on the supply of gas from the primary side and on the flow of diffusion in the filter which may vary from filter to filter under test. Therefore, it is very difficult to accurately read the bubble point from the chart, which results in an impossible validation.

The pressure hold mode is also commonly used in evaluating the membrane filter. In this mode, a gas pressure is supplied to the primary side of a membrane filter to increase the pressure within the space in the primary side of the filter up to a predetermined pressure level. This predetermined level is within the diffusion range; i.e., the range wherein the pressure in the secondary side of the filter increases proportionally to the pressure in the primary side, and below the pressure creating the bubble point. As soon as the testing gas pressure has reached the predetermined level, the supply of gas is stopped, and any changes in the gas pressure in the primary side of the membrane filter is monitored by means of a recorder. For example, after a given initial time period, the reduction of primary side pressure is outputted as a chart which in turn is read by the operator.

In this case, only the gradual pressure reduction is indicated by the chart, irrespective of the capacity, temperature and other factors at the primary side of the membrane filter. However, the filter characteristic is susceptible to variations in these factors. Therefore, the operator must take into account the additional factors in the measuring system to compensate the test results. Even after considering these factors, in such an arrangement of the conventional test method it is considered in the industry that the test results cannot be correlated with the bacteria challenge test. Thus, the validation based on the pressure hold test is impossible.

There is further known in the prior art a diffusion flow type integrity testing system to which the pressure hold testing process is applied. The diffusion flow mode test is another kind of test widely used in the art wherein a constant pressure is applied across the wetted membrane filter and actual flow of gas on the secondary side of the membrane filter is measured. The quantity of gas diffusion is proportional to the pressure differential occurring between primary and secondary sides, and inversely proportional to the thickness of the water layer of membrane filter. For diffusion testing, the pressure applied on the inlet side has to be constant and is lower than that at which the bubble point is reached. The pressure used in this test is, for example, around 80% of that attained by the bubble point testing. The diffusion flow test is considered to be a more accurate test than the other test modes, since the test results in the diffusion flow test has a direct correlation with the bacteria challenge test.

The typical diffusion flow type perfection testing system in the prior art operates in three modes, that is, valve point mode, pressure hold mode and diffusion flow mode. Since measurements are mechanically made in the bubble point mode, less measurement errors result than with manual measurements. However, the measurement errors still remain in this type of system and are recognized to be about plus/minus 0.5 kg/cm$^2$. As of today, since different systems were made by different manufacturers using different principles, there is an extreme confusion when membrane filters to be tested are produced by several different manufacturers. If a validation is to be visually performed while operating the machine, it is difficult to visually judge the bubble point in a cartridge-type filter which typically has a large capacity. Therefore, this bubble point mode should be exclusively used for a disc type filter which has a smaller capacity.

The pressure hold mode also is mechanically performed with fairly small measurement errors in this conventional testing system. However, the pressure hold test process itself is one that correlates with the bacteria challenge test provided by the filter manufacturers is very hardly proven in practice. Thus, the pressure hold test process also is unsuitable for validation.

The diffusion flow mode in this conventional testing system utilizes the aforementioned pressure hold test process to calculate the diffusion flow from various factors such as primary side volume metered by adding a given pressure to the primary measuring line side, pressure drop and so on. The diffusion flow mode in the conventional testing system has the following problems:
a. The diffusion flow testing process ignores an important principle that the primary pressure must be precisely maintained at a specified level.
b. As the predetermined initial time is prolonged, the measurement must be performed at a pressure lower than the specified level, since there is no means provided to keep the pressure in the primary side of the filter constant.
c. If the temperature in the input side of the filter under test increases, the fluid will expand and change the pressure in the primary side of the filter, resulting in an improper measurement.
d. The diffusion flow testing process utilizes a standard function of mechanically determining the volume in the primary side of the membrane filter under test to calculate the diffusion flow. However, this volume measurement also creates an error. Therefore, since the measurement of the diffusion flow is made based on these erroneous measured values, the final test results have a significant inaccuracy. Furthermore, the test results have poor reproducibility.

Therefore, the conventional diffusion flow type test system for the filter integrity cannot be correlated with the bacterial challenge test, and thus validation with sufficient accuracy is not possible. Therefore, there is a need for a membrane filter test system which is capable of accurately testing the membrane filter characteristics, especially the diffusion flow characteristics so that the integrity of the filter can be accurately validated by correlation with the bacteria challenge test.

SUMMARY OF THE INVENTION

It is therefore an object of the present invention to provide a membrane filter integrity test system which can accurately measure the diffusion flow characteristics of the membrane filter based on the theoretical principle of the diffusion test mode.

It is a further object of the present invention to provide a membrane filter integrity test system which is capable of performing various tests for the membrane filter in a short period of time without regard to the capacity or size of the membrane filter under test.

It is also an object of the present invention to provide a membrane filter integrity test system which can perform other test modes including a bubble point test and a pressure hold test more accurately than the conventional test systems.

It is a further object of the present invention to provide a membrane filter integrity test system which can automatically test the diffusion flow of the membrane filter by accurately controlling a pressure at an inlet side of the membrane filter to keep the pressure constant.

It is another object of the present invention to provide a membrane filter integrity test system which can accurately measure the diffusion flow in the membrane filter without regard to the capacity of the filter.

It is another object of the present invention to provide a membrane filter integrity test system which can accurately detect, calculate, monitor and record the variation of pressure in the primary side of the membrane filter.

According to the present invention, a filter test apparatus for testing the integrity or perfection of a membrane filter performs a diffusion flow test and other tests by automatically supplying a precise amount of fluid such as a pressurized gas to the primary side of the membrane filter to be tested. The precise relationship of time versus pressure is controlled by a computer based controller and recorded by a printer connected to the test system. As is well known in the art, prior to the test, the membrane filter to be tested is provided with water or other liquid such as alcohol so that the membrane filter is sufficiently wetted.

The membrane filter integrity test system of the present invention includes a large volume mass-flow controller for rapidly supplying a larger amount of fluid to the primary side of the membrane filter, and a small volume mass-flow controller for supplying a relatively small amount of fluid to the primary side of the membrane filter. The operation of the large volume mass-flow controller is stopped when the pressure at the primary side of said membrane filter reaches a predetermined level. This predetermined pressure is detected by a pressure detecting means which senses the pressure at the primary side of the membrane filter. The pressure sensor responsively generates a detection signal corresponding to the pressure at the primary side of the membrane filter. A main controller responsive to the detection signal from the pressure sensor controls the small volume mass-flow controller in a negative feedback loop manner for supplying the fluid to the primary side of the membrane filter so that the pressure in the primary side of the filter is maintained at the predetermined value.

DETAILED DESCRIPTION OF THE INVENTION

A membrane filter integrity test system of the present invention will be described in detail in the following with reference to the drawings. As described above, the diffusion flow test is considered to be the most reliable test today which can prove direct correlation with the bacteria challenge test. Thus, the membrane filter test system of the present invention is designed to be particularly advantageous in the diffusion flow test mode. Furthermore, the membrane filter test system of the present invention is advantageous in the other test modes including the bubble point test and the pressure hold test as well.

Figure 1:
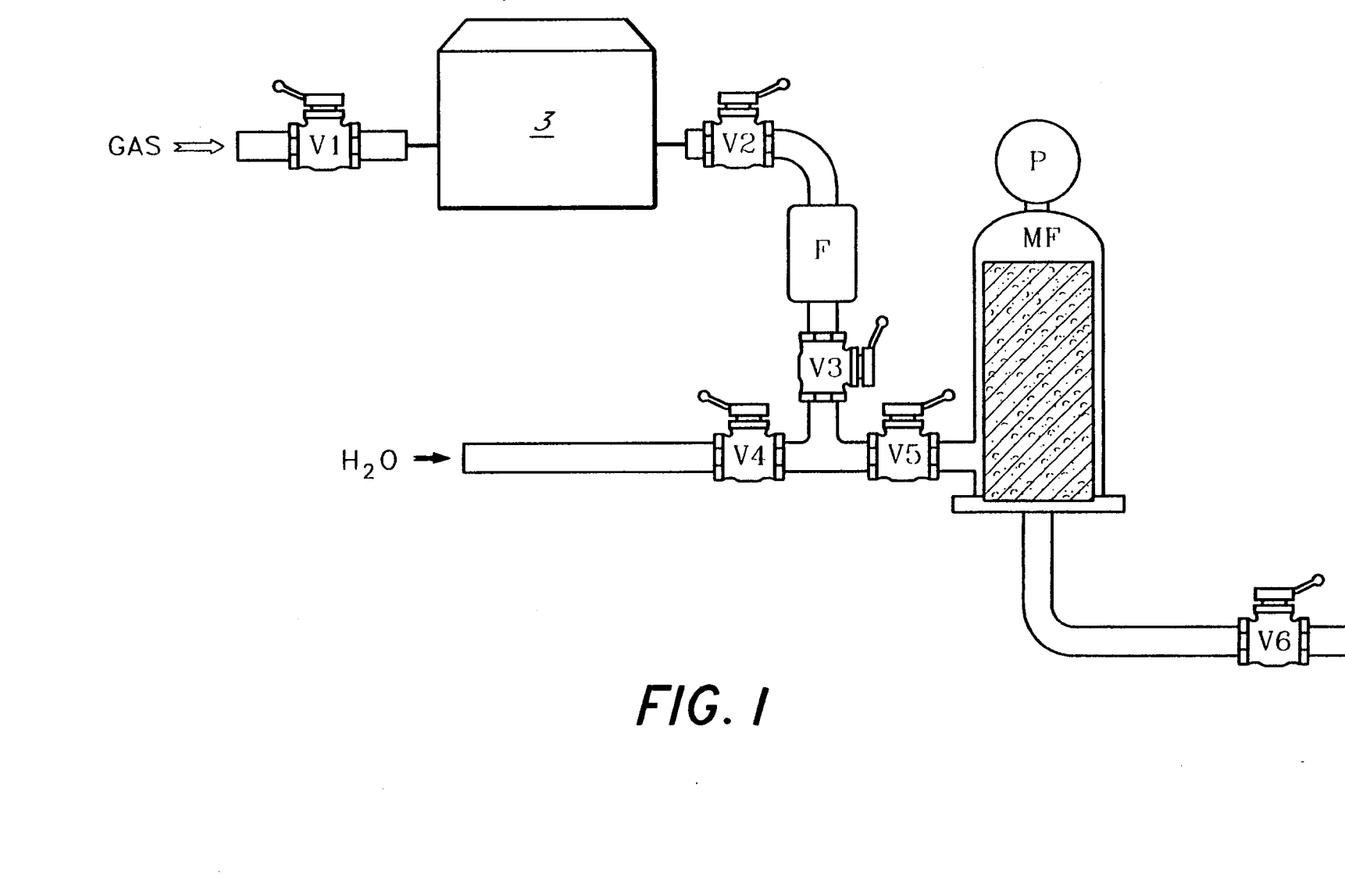
FIG. 1 is a schematic view of an overall configuration for testing a membrane filter integrity by the membrane filter integrity test system in accordance with the present invention.

FIG. 1 shows an example of test configuration in using a membrane filter integrity test system 3 of the present invention. The membrane filter test system 3 is provided with a compressed gas such as air or nitrogen gas at its inlet through a valve V1. The membrane filter test system 3 provides through its output the gas to a primary (inlet) side of a membrane filter MF to be tested. In this example, three valves V2, V3, V5 and a filter F are used on the inlet side of the membrane filter MF; however, those are not always necessary. Usually, in an actual test, at least one valve may be preferably used to control an open/close of the path to the membrane filter MF. The filter F is preferably used in cases where the test environment including the input gas, valves, and the test system 3 may damage a perfect sterilization of the membrane filter MF.

A secondary (outlet) side of the membrane filter MF is connected to, for example, a part of the actual production facility, such as a food production system through a valve V6 in case where the test is undertaken in an active plant (in-line test). Alternatively, the output path may be open or connected to a bubble detector in case where the test is undertaken in a laboratory (off-line test). The membrane filter MF is provided through a valve V4 with liquid such as water or alcohol prior to the test so that the membrane filter MF is sufficiently wet.

The membrane filter MF in FIG. 1 designates a typical cartridge type filter. In the cartridge type filter, the exterior of the cartridge constitutes the primary side of the membrane filter. The primary side of the filter is surrounded by the medium to be filtered. Within the interior, the filtered medium is collected and is drained through bottom end (outlet or secondary) of the membrane filter. As illustrated, a typical cartridge type membrane filter has a pressure meter P. Another type of membrane filter widely used is a disk type filter although not shown in the drawing. The disk type filter is typically a plane, round filter wherein one side of the plane is a primary (inlet) side and the other side is secondary (outlet) side. The cartridge type membrane filter has a larger capacity than the disk type membrane filter.

As will be described in more detail later, an external printer is preferably connected to the membrane filter test system 3 of the present invention. The printer is extremely useful in the membrane filter testing since it can automatically print out, for example, a time versus pressure diagram, which is almost always necessary in the testing. The membrane filter test system 3 of the present invention can also be connected to a remote controller so that the membrane filter testing is performed under the control provided a distance away from the test system.

In operation, the valves 4, 5 and 6 are first opened to provide liquid to the membrane filter MF to be tested. After the membrane filter MF is in a sufficiently wet state, the valve V4 is closed and the liquid is drained in the secondary side of the membrane filter MF through the valve V6. The liquid in the primary side of the membrane filter is also drained through a drainage (not shown) in the primary side of the membrane filter. Then, the valves V2 and V3 are opened to form a pass from the output of the test system 3 to the inlet of the membrane filter MF. The valve V1 is also opened to provide a gas to the input of the test system 3. Prior to the test, an operator provides the membrane filter integrity test system 3 an information for the test through, for example, a keyboard and a display to store the information in a memory. Such information includes the kind of test and test conditions including the type of filter to be tested which will be described in more detail later. The membrane filter test system 3 automatically performs a diffusion flow test and other kinds of test including a pressure hold test and a bubble point test in accordance with the test information stored in the memory of the test system 3. The test results will be displayed in the display of the test system and preferably printed out by the external printer which is connected to the test system 3.

Figure 2:
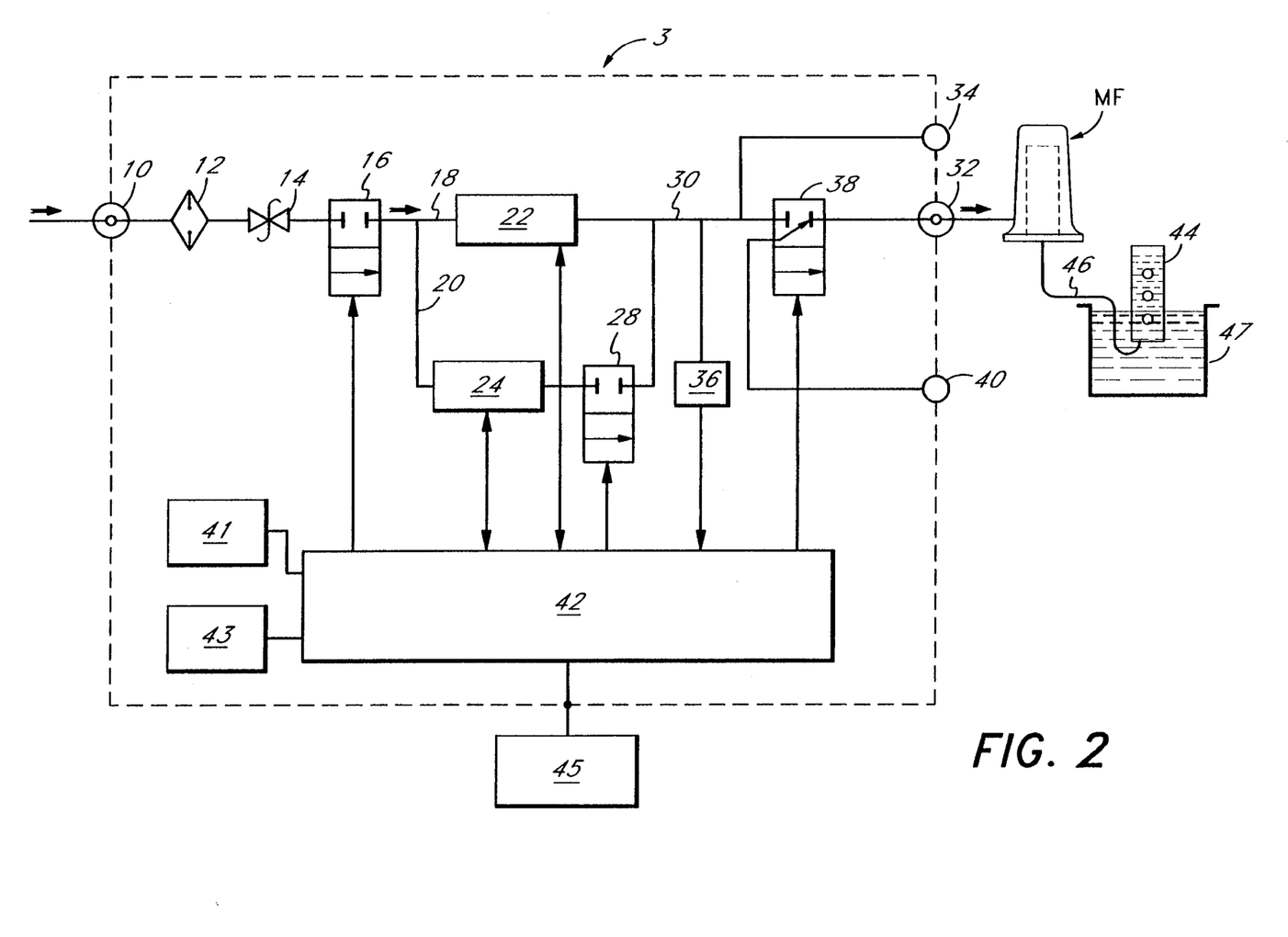
FIG. 2 is a block diagram of one of the embodiments of the membrane filter integrity test system of the present invention.

Referring to FIG. 2, there is shown a membrane filter integrity test system 3 which comprises an inlet 10 for introducing a testing fluid, air or nitrogen gas for example, into the interior of the test system 3. A filter 12 is connected to the inlet 10 to remove unwanted constituents in the gas. A safety valve 14 is preferably connected to the filter 12 for preventing any damages which may be caused by a reverse flow of the gas. A shut-off valve 16 is also connected to the safety valve 14 to form an open and close path for the gas in the downstream. The output side of the shut-off valve 16 is connected to both a small volume mass-flow controller 22 and a large volume mass-flow controller 24 through paths 18 and 20, respectively. A further shut-off valve 28 is located in the downstream of the large volume mass-flow controller 24 to open or close the output supply of the gas from the large volume mass-flow controller 24. In the preferred embodiment, the small volume mass-flow controller 22 can transmit the gas up to 100 cc per minute while the large volume mass-flow controller can transmit the gas up to 5,000 cc per minute.

The paths 18 and 20 merge to a path 30 which receives the gas from the outputs of both the small volume mass-flow controller 22 and large volume mass-flow controller 24. The path 30 connects the output gas from the small volume mass-flow controller and the shut-off valve 28 to a switching valve 38. The switching valve 38 is controlled to open and close a path for the gas to an output connector 32. The path 30 is also connected with exhaust lines which have exhaust terminals 34 and 40 respectively. The exhaust terminal 34 is used for withdrawing the internal gas of the test system 3 while the exhaust terminal 40 is used for withdrawing the external gas, such as in the primary side of the membrane filter. On the path 30, there is also a pressure sensor 36 at an inlet side of the switching valve 38 to detect the gas pressure in the primary side of the membrane filter. A switching valve 38 is connected to the exhaust line 34 at a point downstream of the pressure sensor 36. An accurate pressure sensor suitable for use as the pressure sensor 36 is readily available in the market. The resolution of the pressure sensor for the test system of the present invention is, for example, plus/minus 0.05%. The switching valve 38 is adapted to shut off the exhaust line 34 and to connect the exhaust port 40 with the output connector 32.

All the aforementioned movable parts can be controlled by a main controller 42. The main controller 42 can be any type of micro-controller, such as a 16-bit micro-processor commercially available in the market. The main controller 42 includes a memory (not shown) to store a program for various type of tests. The memory can also store various test information such as test parameters and test conditions provided by an operator. If a memory of larger capacity is necessary, the main controller may be connected with an external memory as is well known in the art. A keyboard 43 and a display 41 are connected to the main controller 42 so that the operator can input instructions or the test conditions by means of the keyboard 43 while monitoring such information on the display 41. The display 41 can also show the test results including the time, pressure amount, the type of test and the like. The main controller 42 also provides an output signal to a printer 45 which is positioned at outside of the membrane filter test system 3. The printer 45 prints out on a paper a diagram showing, for example, a time versus pressure relationship for the membrane filter under test.

The main controller 42 provides control signals to control open and close operations of the shut-off valves 16 and 28 and the switching valve 38. The main controller 42 provides control signals to the small volume mass-flow controller 22 to determine the amount of the gas flow through the small volume mass-flow controller 22. The exact amount of gas flowing through the small volume mass-flow controller 22 is known by the main controller 42 by, for example, a value in the control signal. Similarly, the main controller 42 provides control signals to the large volume mass-flow controller 24 to determine the amount of the gas flow through the large volume mass-flow controller 24. The exact amount of gas flowing through the large volume mass-flow controller 24 is also known by the main controller 42. The pressure sensor 36 supplies a detection signal indicating a pressure amount of the gas at the output of the test system 3, i.e., the inlet of the membrane filter to the main controller 42. As will be described in more detail later, the main controller 42, the large and small volume mass-flow controllers 22, 24 and the pressure sensor 36 constitute a negative feedback loop to accurately and automatically control the gas pressure supplied to the membrane filter under test.

In the example of FIG. 2, the membrane filter MF connected to the output of the membrane filter integrity test system 3 is a cartridge type filter. The membrane filter MF is arranged to undertake the bubble point test, although the diffusion flow test and the pressure hold test also can be performed with this arrangement. The secondary side of the membrane filter MF is introduced to a beaker 47 filled with liquid through a passage 46. The open end of the passage 46 is positioned at the bottom of a cylinder 44 which is also filled with liquid. In this arrangement, if the gas provided at the primary side of the membrane filter MF passes through the filter because the pressure exceeds the bubble point of the filter, the resulting gas in the secondary side is shown as bubbles in the cylinder 44 as illustrated in FIG. 2.

The operation of the membrane filter integrity test system 3 of the present invention is explained below according to FIG. 2. The wetted membrane filer MF to be tested is connected to the output connector 32 of the membrane filter test system 3. A fluid such as air, nitrogen gas and the like is provided at the inlet 10 of the test system 3. Preferably, the maximum pressure of the input gas is around 8.9 bar while the minimum pressure is around 0.5 bar. Then, an operator will input various information regarding the test in the test system 3 through the keyboard 43 and the display 41. Such information includes test conditions such as selection of test program, test date, manufacturer of the filter and serial number and the type and size of the filter to be tested. Further, the information regarding the type of test, a predetermined pressure amount depending on the type of test, the capacity of the membrane filter to be tested, and the pressure hold time and the like are also stored in the test system 3.

By pressing a start key on the keyboard 43, the test system automatically commences the test process according to the program stored in the main controller 42. During the test, the display 41 indicates that the test is under progress by illuminating a test sign. At the end of the test, the display 41 shuts off the illumination to notify the operator the completion of the test. After starting the test, the shut-off valve 16 is first actuated to connect the inlet 10 with the paths 18 and 20. The small volume mass-flow controller 22 and the large volume mass-flow controller 24 are respectively given amounts of gas flow therethrough by the main controller 42. For example, the large volume mass-flow controller 24 is set to 5,000 cc/minute and the small volume mass-flow controller 22 is set to 100 cc/minute. However, these amount are not fixed but may vary depending on the control signal from the main controller 42. The mass-flow controllers 22 and 24 are controlled by the main controller 42 and the pressure sensor 36 in a proportional-plus-integral control manner which is typically used in an automatic control technology and the details of which will be described later.

The pressurized gas is rapidly supplied to the interior of the membrane filter test system 3 through the inlet 10. The shut-off valve 28 is controlled to connect the output of the large volume mass-flow controller 24 with the path 30. The switching 38 is actuated to connect the path 30 to the output connector 32 to provide the gas to the primary side of the membrane filter MF to be tested. Thus, the pressure in the primary side of the membrane filter MF rapidly will increase since the large volume mass-flow controller 24 can send a larger volume of gas to the membrane filter within a short period of time.

The pressure in the primary side of the membrane filter MF is constantly monitored by the pressure sensor 36 which transmits the measured data to the main controller 42. After reaching the predetermined pressure in the primary side of the membrane filter, the large volume mass-flow controller 24 stops supplying the gas based on the instruction from the main controller 42. At the same time, the shut-off valve 28 is closed by the command signal from the main controller 42. The time required to reach the predetermined pressure depends on the capacity of the membrane filter under test and the volume of the mass-flow controller 24. The small volume mass-flow controller 22 continues to send a small amount of gas to the primary side of the membrane filter MF in the diffusion flow test mode and the bubble point test mode to maintain the pressure in the primary side of the membrane filter under test at a constant amount. However, the operation of the small volume mass-flow controller 22 will be terminated in the pressure hold test mode.

As described above, in the diffusion flow mode, the small volume mass-flow controller 22 is controlled to maintain the predetermined pressure after the primary side of the membrane filter under test reaches the predetermined pressure amount. This procedure in the present invention is important since the pressure in the primary side of the membrane filter under test will decrease because of the diffusion of the gas through the pores of the filter. Further, the theoretical bases of the diffusion test requires that the pressure in the primary side of the filter be fixed to the predetermined value and maintained at the same value during the test. In the present invention, the pressure sensor 36 detects the current pressure in the primary side of the membrane filter MF and the main controller determines the amount of gas flow from the small volume mass-flow controller 22 to supplement the pressure decrease.

Thus, the balance between the flow supply and the diffusion flow can be maintained at an increased accuracy. For example, a larger capacity filter housing or filter having an increased diffusion flow may have an increased flow supply while a smaller capacity filter housing or filter having a decreased diffusion flow may have a decrease flow supply. According to the membrane filter test system 3 of the present invention, it is possible to maintain the pressure constant with high accuracy without regard to the differences in type and size of the membrane filter under test. The negative feedback loop formed by the pressure sensor 36, the main controller 42 and the small volume mass-flow controller 22 proportionally amplifies a difference between the predetermined pressure and the current pressure in the primary side to control the supply of gas. As is well known in the automatic control technology, the proportional-plus-integral control serves to prevent any oscillation (disturbance in data) in the feedback loop.

As described above with respect to the background of the invention, the diffusion flow mode test is a test wherein a constant pressure is applied across the wetted membrane filter and actual flow of gas on the secondary side of the membrane filter is measured. The quantity of gas diffusion is proportional to the pressure differential occurring between primary and secondary sides, and inversely proportional to the thickness of the water layer of membrane filter. Thus, for obtaining the diffusion flow (quantity of gas diffusion through the filter under test) in the membrane filter test system 3 of the present invention, the gas flow supplemented by the small volume mass-flow controller is monitored by the main controller 42. The gas flow value within a certain period of time, i.e., cc/minute under the predetermined pressure represents the diffusion flow of the membrane filter under test.

It is preferable to perform the diffusion flow test first and move to the bubble point test, since the bubble point of the membrane filter comes after the diffusion flow, by further increasing the pressure in the primary side of the filter. More specifically, the pressure applied on the primary side in the diffusion flow test is, for example, around 80% of that will be attained by the bubble point testing. Thus, by increasing the gas pressure at the primary side of the membrane filter MF, the bubble point test can automatically be conducted in the membrane filter test system 3 of the present invention.

For example, if the capacity of the membrane filter under test is large, the large volume mass-flow controller 24 is activated to provide a large amount of gas flow so that the pressure in the primary side of the filter quickly comes close to the bubble point. Then, the operation of the large volume mass-flow controller 24 is terminated and the small volume mass-flow controller 22 will gradually supply the gas to the membrane filter under test. The bubble point of the filter under test is detected by precisely and slowly increasing the gas pressure in the primary side of the filter using the small volume mass-flow controller 22 which generates a gas flow of, for example, 25 cc/minute. The fine increase of pressure by the small volume mass-flow controller 22 is especially helpful for testing a membrane filter of small capacity, a disk type membrane filter, for example.

Thus, by observing the first bubble apparent in the cylinder 44, the bubble point can be obtained by recording the gas pressure in the primary side of the membrane filter. This pressure amount is accurately measurable, since the pressure sensor 36 accurately detects the pressure and the main controller 42 controls the gas flow from the mass-flow controller to maintain the precise pressure based on the pressure data from the pressure sensor 36. As described with respect to the background of the invention, the conventional test technology cannot measure the bubble point accurately, since it does not have a pressure control means which can maintain the pressure constant as in the present invention. In particular, when testing a membrane filter of relatively large capacity, a significant amount of diffusion flow will start before the bubble point is reached so that the gas pressure in the primary side will decrease in the conventional test system. This problem will be overcome by the present invention since the test system 3 can accurately control the pressure on the primary side of the membrane filter MF.

The pressure hold mode test can also be performed by the membrane filter integrity test system 3 of the present invention. The pressure hold test by the membrane filter test system 3 is performed in the same way as proceeded in the conventional test system. Namely, the predetermined gas pressure is given to the primary side of the membrane filter and after a certain period of time, for example, 300 seconds, has elapsed, the pressure decrease in the primary side is measured by the pressure sensor 36.

As seen in the foregoing, the combination of the large and small volume mass-flow controllers in the membrane filter test system 3 of the present invention is advantageous since this combination functions as both coarse tuning and fine tuning of the gas pressure. The coarse tuning contributes to a reduction of time for the test, while the fine tuning increases the accuracy of the test. An experiment under the arrangement of the present invention proves that the test processes can provide accurate data with higher stability for various types of membrane filter. If a capacity of the filter to be tested is extremely large, an additional large volume mass-flow controller may be provided to the test system. Under the combination of the large and small volume mass-flow controller of the present invention, almost all the measurement can be made within several minutes. Moreover, the measurement error can be maintained dramatically low, for example, the precision of the pressure measurement is within one cc/minute.

Throughout the above-mentioned tests, the printer 45 records the test results including the pressure curve, time sequence from the start of test in addition to the general information regarding the filter under test. Since the pressure changes, and the associated curve of increasing pressure from the start of measurement to the termination thereof, are sampled at accurate time intervals, the point of change for determining the bubble point, for example, can be easily detected.

Figure 3:
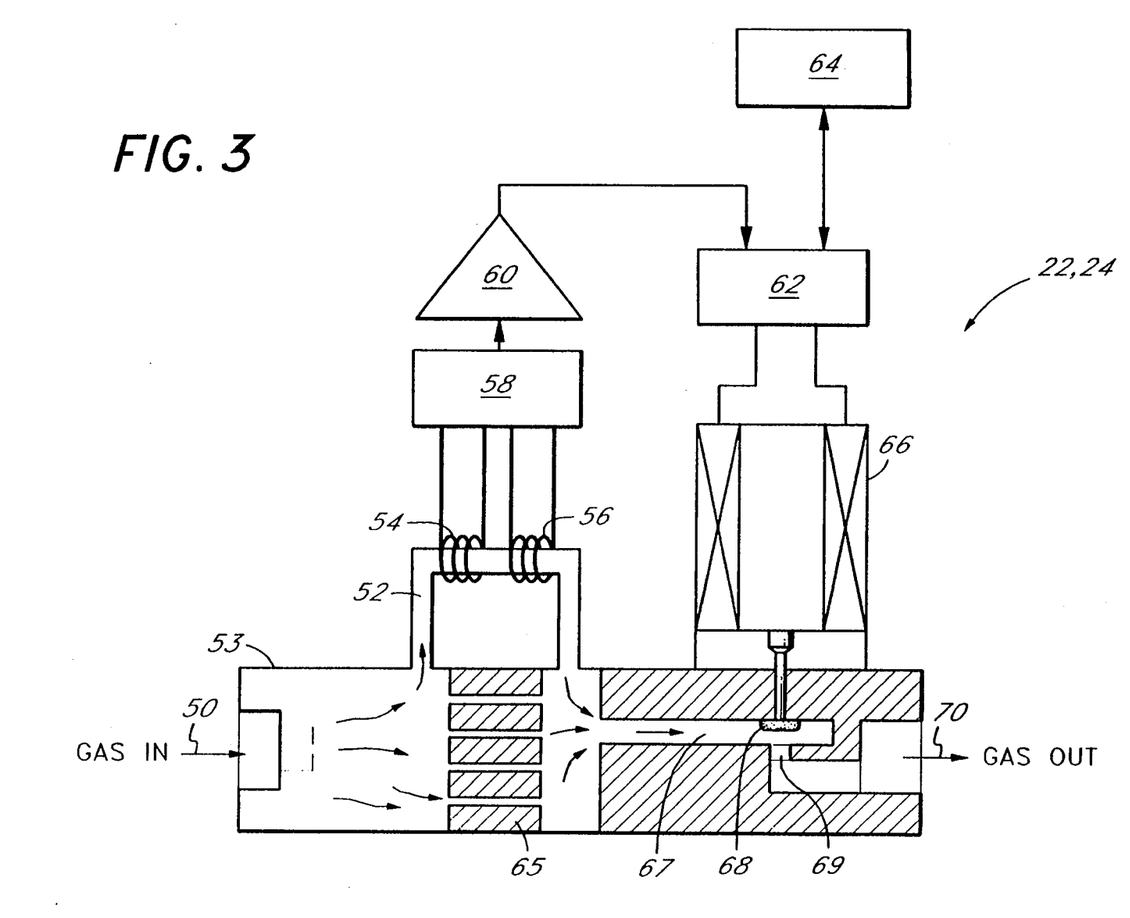
FIG. 3 is a block diagram of an example of mass-flow controller preferably used in the membrane filter test system in accordance with the present invention.

FIG. 3 shows an exemplary block diagram of the mass-flow controllers 22 and 24 of the present invention. The structure of the mass-flow controller is basically the same for the small volume and large volume mass-flow controllers except for differences in size. The mass flow controller 22 or 24 is formed of a housing 53 having an inlet 50 and an outlet 70. The housing 53 further includes a capillary 52, a manifold 65 and a passage 67 and a nozzle 69. A valve 68 is provided within the housing 53 to control the gas flow of the nozzle 69. Two thermal resistance wires 54 and 56 are connected across the capillary 52 whose resistances vary, depending on the temperature difference in the capillary 52 caused by the flow of gas. The other ends of the thermal resistance wires 54 and 56 are connected to a bridge circuit 58 which detects the difference of the resistance value in the thermal resistance wires 54 and 56 and generates a corresponding electric signal at its output. An amplifier 60 amplifies the output signal from the bridge circuit 58 and supplies its output to a comparator circuit 62. The other input terminal of the comparator circuit 62 is connected to a register 64 which stores flow data from the main controller 42 and generates a corresponding analog voltage to the comparator circuit 62. The comparator circuit 62 generates an electric current to a solenoid 66 which drives the valve 68 depending on the value of the current.

In operation, the input gas flows through the manifold 65 to the passage 67 and the nozzle 69 through a gap formed between the valve 68 and the nozzle 69. The gas passes through the gap is outputted at the outlet 70. A part of the gas flows through the capillary 52 and merges with the gas from the manifold 65. The gas which is flowing through the capillary 52 causes a difference in temperature between the two positions where the thermal resistance wires 54 and 56 are located. The difference in the temperature varies depending on the amount of gas flow in the capillary 52.

The difference of the temperature is sensed by the resistance change in the thermal resistance wires 54 and 56, and converted to the electric signal by the bridge circuit 58 and compared with the reference value from the register 64 by the comparator circuit 62. The valve 68 is controlled to compensate the difference between the two inputs of the comparator circuit 62. As a result, the gas flow from the outlet 70 of the mass-flow controller is accurately controlled by the flow data stored in the register 64 which is provided from the main controller 42 of FIG. 2. The main controller 42 will change the flow data in the register 64 depending on the gas pressure in the primary side of the membrane filter detected by the pressure sensor 36 in FIG. 2.

As has been described in the foregoing, according to the present invention, the membrane filter integrity test system can accurately measure the characteristics of the membrane filter in a short period of time without regard to the capacity or size of the membrane filter under test.

What is claimed is:

1. An apparatus for testing the perfection of a membrane filter, said apparatus comprising:
   a large-flow controller for supplying a primary side of said membrane filter rapidly with a larger amount of a fluid;
   a pressure detecting sensor for detecting the pressure at said primary side of said membrane filter and for responsively generating a detection signal;
   a small-flow controller for supplying the primary side of said membrane filter with a smaller amount of said fluid;
   a switching member for forming a fluid path for said fluid from said large-flow controller and said small-flow controller to said membrane filter, said switching member disconnecting said fluid path and forming an exhaust path for withdrawing said fluid in said primary side of said membrane filter
   a main control unit responsive to the detection signal from said pressure detecting sensor to stop the operation of said large-flow controller when the pressure at the primary side of said membrane filter reaches a predetermined level, the main control unit then controlling said small-flow controller in a proportional/integral control manner to compensate the pressure decrease caused by said membrane filter to maintain said predetermined level, said main controller monitoring the amount of fluid flowing from said small-flow controller to said membrane filter to determine diffusion flow in said membrane filter.

2. The apparatus of claim 1, wherein said fluid is a gas and each of said large-flow controller and said small-flow controller comprises:
   a housing having an inlet and an outlet;
   a manifold within said housing through which a main stream of fluid flows;
   a capillary through which a secondary stream of fluid flows from an upstream side of said manifold to a downstream side of said manifold; and
   two thermal resistance wires mounted at two spaced positions along said capillary,
wherein a temperature difference in the secondary flow at the two positions where the thermal resistance wires are located is sensed by a resistance change in the thermal resistance wires in order to determine the gas flow through the large-flow controller and the small-flow controller.

3. The apparatus of claim 2 further comprising a register which stores flow data from the main control unit, wherein the main control unit changes the flow data in the register depending on the gas pressure on the primary side of the membrane filter detected by the pressure detecting sensor.

4. The apparatus of claim 3, wherein each of said large-flow controller and said small-flow controller further including:
   a bridge circuit connected to the ends of the thermal resistance wires which detects the difference of the resistance value in the thermal resistance wires and generates a corresponding electric output signal;

an amplifier which amplifies the output signal from the bridge circuit to output an amplified signal;

a comparator circuit which receives the amplified signal from the amplifier and also a reference signal from the register;

a valve which opens or closes a gap provided in proximity to said outlet; and a solenoid for actuating said valve, wherein the comparator circuit compares the amplified signal with the reference signal and generates an electric current to the solenoid which actuates the valve to compensate for the difference between the two input signals of the comparator circuit.

5. A method for testing the integrity of a membrane filter, said method comprising the steps of:

supplying a fluid to a membrane filter test system through an inlet valve;

allowing said fluid to contact a primary side of said filter until completely wetted;

closing said valve to shut off said supply of fluid;

draining said fluid from the system;

supplying a gas to said membrane filter test system through a second inlet valve on the primary side of the filter;

monitoring a pressure on the primary side of said filter with a sensor which generates a pressure signal;

transmitting the pressure signal to a main controller;

commencing a first gas flow to the primary side of the membrane filter through a large-flow controller;

stopping said first gas flow by actuating a valve within said large-flow controller based on instructions from the main controller when a predetermined pressure on the primary side of said membrane is reached;

delivering a second gas flow to the primary side of the membrane filter through a small-flow controller;

maintaining a predetermined pressure in the primary side of the membrane filter during the test by metering flow through said small-flow controller based on a feedback loop comprised of said sensor, said main controller and said small-flow controller.

6. The method of claim 5, wherein a bubble point test is conducted, the bubble point test comprising the steps of:

diverting an outlet flow line from a secondary side of said filter to a reservoir of liquid;

transmitting said pressure signal to an output recorder for creating a record of the time-varying pressure signal;

increasing the pressure on the primary side of said membrane filter by actuating said small-flow controller past a point at which bubbles are apparent in the reservoir;

comparing said pressure-signal record with the time when bubbles were apparent to determine the bubble point of said filter.

* * * * *